(12) United States Patent
Maharajh et al.

(10) Patent No.: US 8,634,709 B2
(45) Date of Patent: Jan. 21, 2014

(54) CAPILLARY SYSTEM WITH FLUIDIC ELEMENT

(75) Inventors: Niranjan Maharajh, Broomfield, CO (US); Gene Faison, Richmond, VA (US); Sudarsan Srinivasan, Glen Allen, VA (US); David Ammann, Richmond, VA (US); Donald Brookman, Richmond, VA (US); Amit Limaye, Napa, CA (US); Ronald Formosa, Jr., Mechaniscsville, VA (US)

(73) Assignee: Philip Morris USA Inc., Richmond, VA (US)

( * ) Notice: Subject to any disclaimer, the term of this patent is extended or adjusted under 35 U.S.C. 154(b) by 1137 days.

(21) Appl. No.: 12/285,312

(22) Filed: Oct. 1, 2008

(65) Prior Publication Data

US 2009/0310950 A1 Dec. 17, 2009

Related U.S. Application Data

(60) Provisional application No. 60/976,998, filed on Oct. 2, 2007.

(51) Int. Cl.
*F22B 29/06* (2006.01)
*B01D 3/06* (2006.01)

(52) U.S. Cl.
USPC .................... 392/397; 392/385; 392/399

(58) Field of Classification Search
None
See application file for complete search history.

(56) References Cited

U.S. PATENT DOCUMENTS

| 4,575,609 | A |  | 3/1986 | Fassel et al. |
| 4,960,992 | A |  | 10/1990 | Vestal et al. |
| 5,743,251 | A | * | 4/1998 | Howell et al. ............ 128/200.14 |
| 6,003,512 | A |  | 12/1999 | Gerde |
| 6,276,347 | B1 |  | 8/2001 | Hunt |
| 6,501,052 | B2 |  | 12/2002 | Cox et al. |
| 6,640,050 | B2 |  | 10/2003 | Nichols et al. |
| 6,772,757 | B2 |  | 8/2004 | Sprinkel, Jr. |
| 6,804,458 | B2 |  | 10/2004 | Sprinkel, Jr. et al. |
| 6,883,516 | B2 | * | 4/2005 | Hindle et al. ............ 128/200.14 |
| 7,128,067 | B2 | * | 10/2006 | Byron et al. ............. 128/200.14 |
| 7,147,170 | B2 | * | 12/2006 | Nguyen et al. .................. 239/13 |

(Continued)

FOREIGN PATENT DOCUMENTS

| DE | 1077828 B | 3/1960 |
| EP | 0624379 A | 11/1994 |

(Continued)

OTHER PUBLICATIONS

International Search Report and Written Opinion mailed Mar. 17, 2009 for PCT/IB2008/003258.

(Continued)

*Primary Examiner* — Thor Campbell
(74) *Attorney, Agent, or Firm* — Buchanan Ingersoll & Rooney PC (57) ABSTRACT

An aerosol generation system having an aerosol generator wherein a liquid formulation is at least partially volatilized in a capillary passage and discharged from the capillary passage to form an aerosol. The aerosol generation system includes a pumping unit adapted to supply a liquid formulation to the aerosol generator; and a fluidic element located between the pumping unit and the capillary passage of the aerosol generator, wherein the fluidic element increases backpressure of the liquid formulation as the liquid formulation enters the capillary passage of the aerosol generator.

21 Claims, 12 Drawing Sheets

(56) References Cited

U.S. PATENT DOCUMENTS

| | | |
|---|---|---|
| 7,167,776 B2 | 1/2007 | Maharajh et al. |
| 7,173,222 B2 | 2/2007 | Cox et al. |
| 2002/0079309 A1 | 6/2002 | Cox et al. |
| 2003/0108342 A1 | 6/2003 | Sherwood et al. |
| 2004/0223918 A1 | 11/2004 | Pham et al. |
| 2005/0000512 A1 | 1/2005 | Ganan-Calvo |
| 2005/0229926 A1 | 10/2005 | Fink et al. |
| 2005/0235991 A1 | 10/2005 | Nichols et al. |
| 2006/0163570 A1 | 7/2006 | Renn et al. |
| 2008/0087280 A1* | 4/2008 | Dhuper et al. ........... 128/200.23 |

FOREIGN PATENT DOCUMENTS

| | | |
|---|---|---|
| FR | 2543442 A | 10/1984 |
| SU | 546353 A1 | 2/1977 |
| WO | WO97/42993 A | 11/1997 |
| WO | WO01/38514 A | 5/2001 |
| WO | WO03/012565 A | 2/2003 |
| WO | WO03/053502 A | 7/2003 |
| WO | WO2004/022242 A | 3/2004 |
| WO | WO2005/003547 A | 1/2005 |
| WO | WO2005/106350 A | 11/2005 |
| WO | WO2004/076064 A | 7/2007 |
| WO | WO2007/102087 A | 9/2007 |
| WO | WO2008/042912 A | 4/2008 |

OTHER PUBLICATIONS

International Preliminary Report on Patentability issued Apr. 7, 2010 for PCT/IB2008/003258.

* cited by examiner

Table: Particle Size Data in D90 (wherein D90 is the size at which 90 percent of the particles are below the stated particle size)

|  | D90, μm: Before fluidic element | D90, mm: After fluidic element |
|---|---|---|
|  | 114 | 43 |
|  | 85 | 30 |
|  | 102 | 29 |
|  |  | 33 |
|  |  | 38 |
|  |  | 33 |
| Average | 100 | 34 |

FIG. 14 ern embodiment.

CAPILLARY SYSTEM WITH FLUIDIC ELEMENT

CROSS-REFERENCE TO RELATED APPLICATION

This application claims priority to U.S. Patent Provisional Application No. 60/976,998, filed Oct. 2, 2007, which is incorporated herein by this reference in its entirety.

BACKGROUND

Capillary aerosol technology and capillary aerosol generators have been described in U.S. Pat. No. 5,743,251, the contents of which are hereby incorporated by reference in their entirety.

SUMMARY

In accordance with one embodiment, an aerosol generation system, comprises: an aerosol generator wherein a liquid formulation is at least partially volatilized in a capillary passage and discharged from the capillary passage to form an aerosol; a pumping unit adapted to supply a liquid formulation to the capillary passage of the aerosol generator; and a fluidic element located between the pumping unit and the capillary passage of the aerosol generator, wherein the fluidic element increases the backpressure of the liquid formulation as the liquid formulation enters the capillary passage.

In accordance with a further embodiment, a method of producing an aerosol comprises: supplying a liquid material to a heated capillary passage at a flow rate of 20 µl/s such that a pressure of the liquid at an inlet to the capillary passage is at least 1000 psi (pounds per square inch); and generating an aerosol with the heated capillary.

DETAILED DESCRIPTION

Aerosols are useful in a wide variety of applications. For example, it is often desirable to treat respiratory ailments with, or deliver drugs by means of, aerosol sprays of finely divided particles of liquid and/or solid, e.g., powder, medicaments, etc., which are inhaled into a patient's lungs. Aerosols can be generated from a heated capillary aerosol generator by feeding a solution or suspension in a liquid state (i.e., a liquid formulation or liquid material) to a capillary while heating the capillary sufficiently such that the solution (or the carrier portion of the suspension) is volatilized, so that upon discharge from the heated capillary, the solution (or suspension) is in the form of an aerosol. The length of the capillary can depend on heat requirements dictated by, among other factors, the composition of the aerosol to be generated. A potential problem associated with directly heated capillary aerosol generators is broad temperature variations inside the capillary tube that may lead to overheating and substandard aerosol formation, resulting in clogging of the capillary tube and/or failure of the capillary aerosol generator.

It can be appreciated that an aerosol generation system can be used to aspirate a liquid material or formulation from a container closure system, and dispense it through an aerosol generator or capillary tube sub-assembly for delivery of a continuous aerosolization. It would be desirable to improve the reliability and the robustness of the capillary aerosol generation system by having a system and method, which can stabilize the nominal operating pressure within the capillary passage of an aerosol generation unit by increasing the threshold backpressure for aerosolization (i.e., the minimum pressure needed to keep the flow consistent and capillary wet) and reduces the pressure oscillation within the system as a result of the conversion of the liquid material or formulation to vapor and large particles within the liquid material or formulation.

In accordance with one embodiment, a fluidic element is located between a pumping unit and a capillary tube of an aerosol generator, wherein the fluidic element increases the backpressure of the liquid formulation, such that the thermally conductive heater block maximizes heat transfer substantially evenly and uniformly from the thermally conductive heater block to the capillary tube.

In operation, electrical leads transfer power from a power source to heater cartridges that are inserted into the thermally conductive heater block, thereby heating the thermally conductive heater block. When heated, the thermally conductive heater block transfers heat to the aerosol generation unit or capillary tube and thus substantially evenly and uniformly heats the capillary tube to a temperature sufficient to at least partially volatilize the liquid material or the liquid formulation that is introduced to the heated capillary tube. For example, the at least partially volatilized liquid material or liquid formulation can be driven through a restrictor to atomize the liquid material or formulation. The volatilized material mixes with air supplied by a heated sheath air source within an aerosol confinement member at a distal end of the heater block and forms an aerosol.

Figure 1:
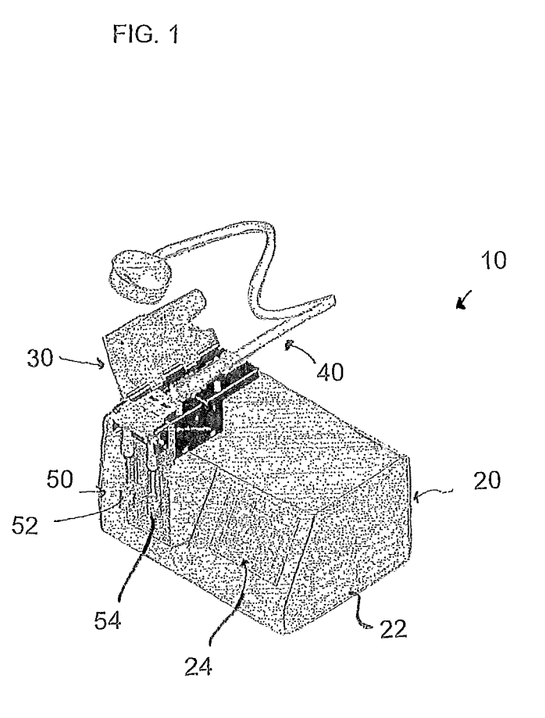
FIG. 1 is a perspective view of an aerosol generation system in accordance with one embodiment having a heater block in an open position.

Referring to FIG. 1, in accordance with one embodiment, a perspective view of an aerosol generation system 10 is shown. Liquid formulation or liquid material is preferably introduced into a capillary tube through an inlet of the capillary tube connected to a source of liquid material. The volatilized material is driven out of the capillary tube through the outlet of the capillary tube, i.e., pressure of liquid from the source of liquid material, which causes the liquid to be ejected from the outlet.

In accordance with one embodiment, as shown in FIG. 1, an aerosol generation system (or drug delivery system) 10 having an aerosol generator and a heater block, the temperature of the heater block and the thermally conductive material is heated to and maintained at an operating temperature (i.e., a temperature at which liquid material in the capillary tube is volatilized), which can be in the range of about 250° C. to 400° C. However, when the aerosol is generated with this aerosol generation system 10, the system 10 may generate significant backpressure (i.e., the pressure within the system from the outlet or reduced orifice at the exit of the capillary or capillary tube of the aerosol generation unit to the syringe pumps) in the order of 600-900 psi, due to vaporization of the liquid formulation and the pumping of the vapor/liquid through the reduced orifice at the exit of the aerosol generator. In addition, the system 10 may experience inconsistent flow in the capillary, large particles in the formulation, and suboptimal vaporization, which can cause sudden pressure spikes in the system 10 in the order of 2000-3000 psi.

The system 10 can also experience variations in nominal pressure within the capillary or capillary passage from run to run (within a unit), oscillations in pressure profiles, clogging of the exit orifice with nominal pressures below 1000 psi, and particles with sizes that are greater than the diameter of the exit orifice in the capillary system 10. For example, when the nominal pressure is below 1000 psi, the system 10 may experience a pulsating aerosol, which results in capillary operating pressure spikes. In addition, when these pressure spikes occur, the aerosol generation system 10 may not be capable of withstanding such high pressures and results in a clogging of the capillary. The disposable delivery packet components and the fittings that are in the delivery packet fail when a failure occurs, which results in non-operation of the unit. Accordingly, it would be desirable to provide a system and method for improving the reliability and the robustness of the capillary aerosol generator, wherein a liquid formulation is partially vaporized to form an aerosol for inhalation.

As shown in FIG. 1, the aerosol generation (or drug delivery) system 10 comprises a base unit 20, which is adapted to receive a disposable assembly 40 in the form of a sterile disposable fluid system. The base unit 20 is comprised of a housing 22, a disposable assembly housing 30 adapted to receive the disposable assembly 40, and a compact reconfigurable input/output (I/O) controller assembly (not shown) and user interface 24. The user interface 24 can be a touch screen panel as shown in FIG. 1, or other suitable interface system for input of information and receiving of operational data from the system 10. The disposable assembly housing 30 is preferably comprised of a clam-shell like housing, which is adapted to receive the disposable assembly 40 having an aerosol generation unit (or aerosol generator) 90 and a fluidic element 100. As shown in FIG. 1, the disposable assembly housing 30 in the base unit 20 is comprised of an upper or first half and a lower or second half, which is adapted to surround the disposable assembly 40 in a clam-shell configuration, including a handle for ease of opening and closing of the housing 30. The disposable assembly 40 fits within the lower or second half of the housing 30, and ensures that the components of the disposable assembly 40 are matched to their respective connections within the base unit 20.

In use, the aerosol generation unit 90 can include an indirect heating block assembly (not shown), which encases a heated capillary tube, heats a liquid material or liquid formulation 26, which is pumped through the aerosol generation unit at a constant and continuous rate by a pumping unit 50. The pumping unit 50 preferably includes two syringe pumps 52, 54 and a valving arrangement or assembly 60 (FIG. 3) operable to supply liquid formulation into an inlet of one syringe pump 52, 54 during delivery of liquid formulation to the aerosol generation unit by the other syringe pump 52, 54. In accordance with one embodiment, the pumping unit 50 and valving arrangement 60 continuously deliver the liquid formulation 26 to the capillary at approximately 15 to 25 microliters per second ($\mu l/s$), and more preferably about 18 to 22 microliters per second ($\mu l/s$), and most preferably about 20 microliters per second ($\mu l/s$).

Figure 2:
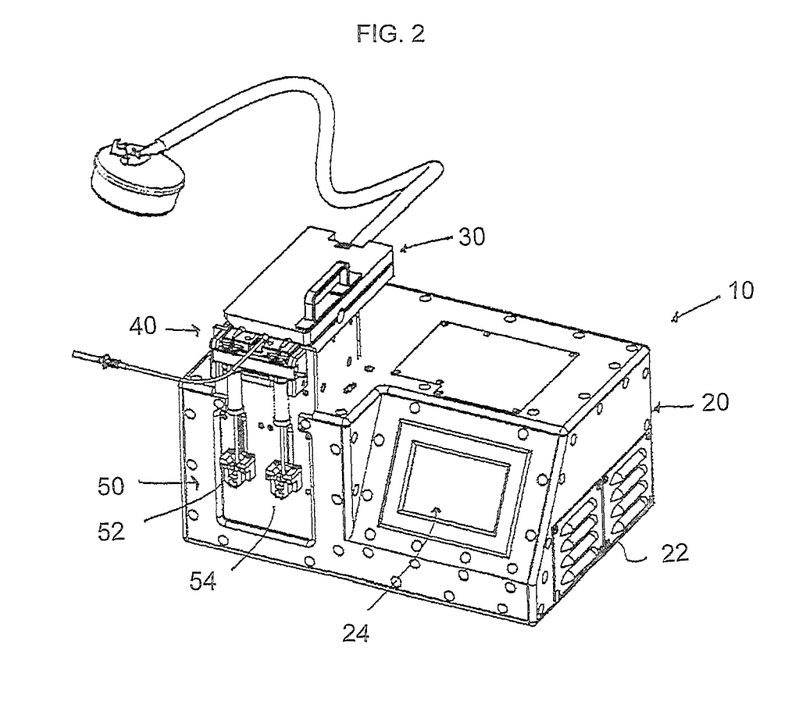
FIG. 2 is a perspective view of the aerosol generation system of FIG. 1 with the heater block in a closed position.

FIG. 2 is a perspective view of the aerosol generation system 10 of FIG. 1 with the disposable assembly housing 30 in a closed position. The disposable assembly 40 is attachable to a source of liquid material or liquid formulation 26, which is partially volatilized to form an aerosol. The capillary aerosol generation system 10 is adapted to continuously deliver a liquid material or liquid formulation as an aerosol, wherein the liquid material or formulation 26 is heated in an aerosol generation unit 90 to partially volatilize at least some of the liquid material or liquid formulation 26. The aerosol generation system 10 can be comprised of a base unit 20 and wetted components including a sterile disposable fluid system or disposable assembly 40.

Figure 3:
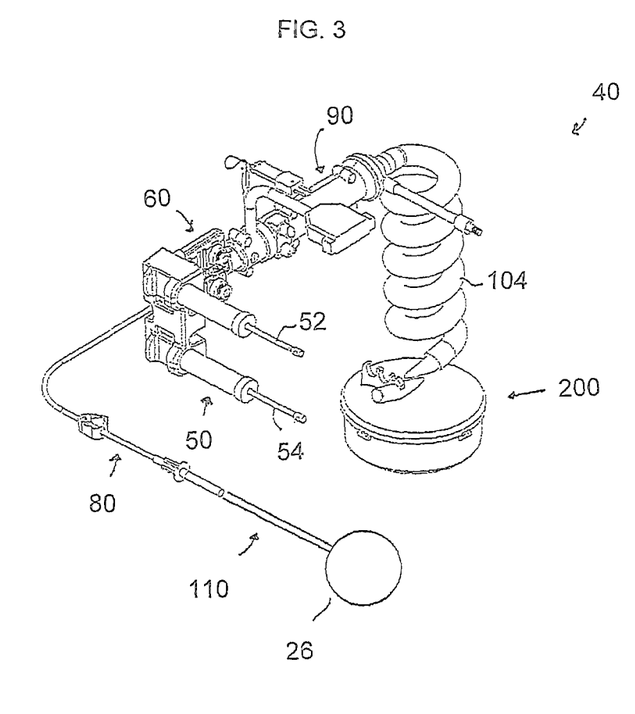
FIG. 3 is a perspective view of a disposable assembly of the aerosol generation system of FIG. 1.
Figure 13:
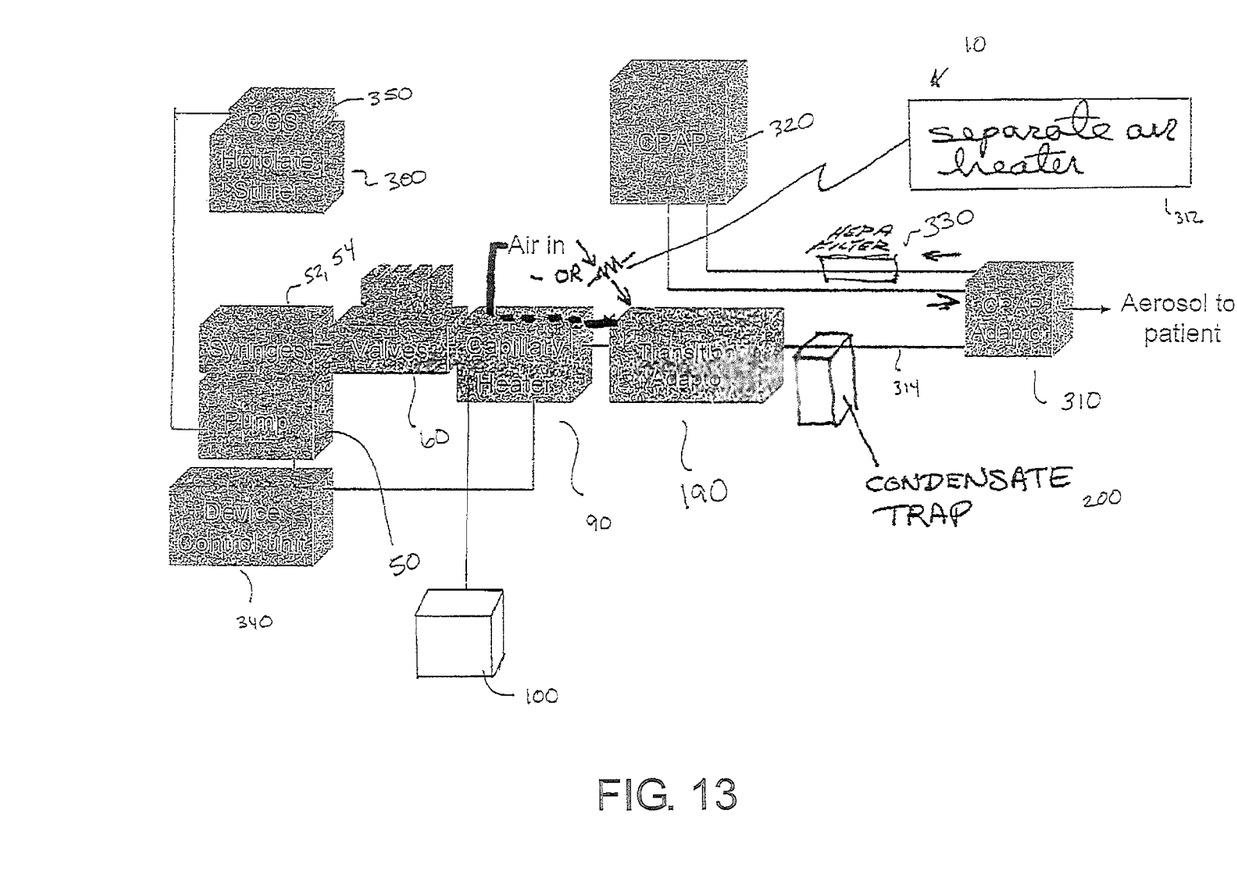
FIG. 13 is a diagram of an aerosol generation system in accordance with one embodiment.
Figure 14:
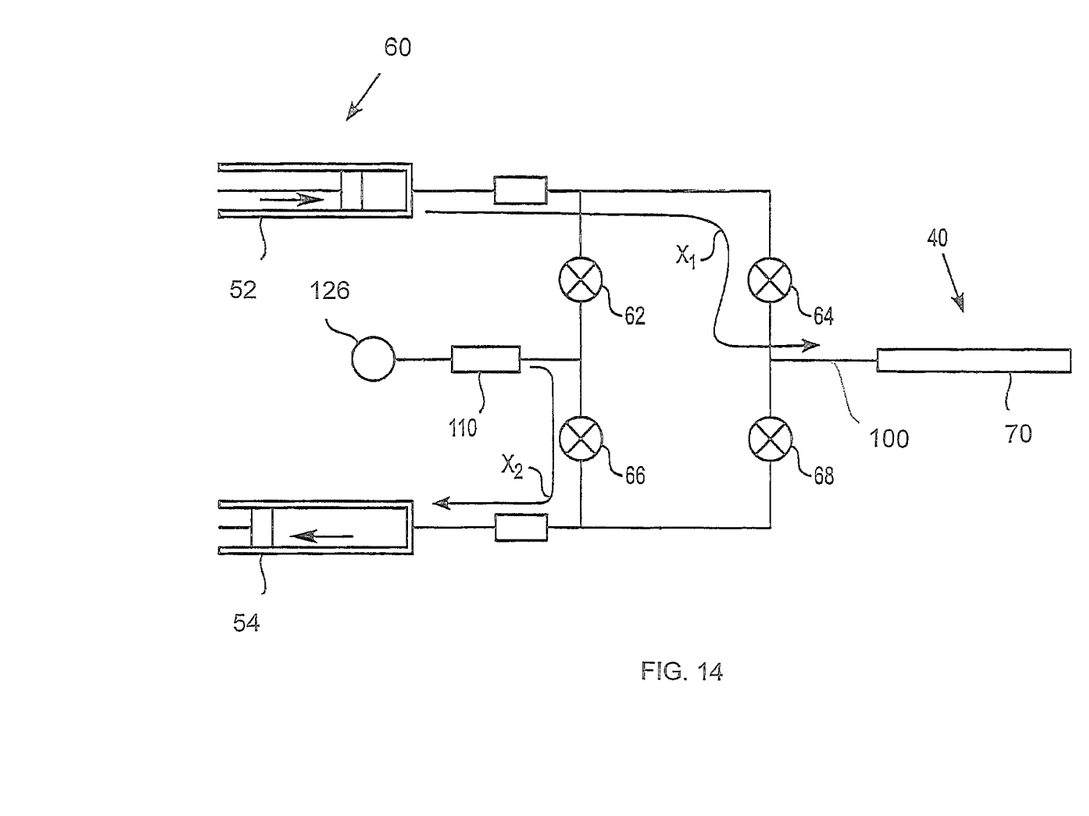
FIG. 14 is a schematic diagram of a valving assembly and a fluidic element in accordance with an embodiment.

Referring to FIGS. 3 and 14, the disposable assembly 40 preferably includes a valve assembly (or valving arrangement) 60, an input fluid tube assembly 80, an aerosol generation unit 90, and a fluidic element 100. The valve assembly 60 preferably includes a plurality of valves 62, 64, 66, 68. The fluidic element 100 is located between valves 64, 68 and a heated capillary passage 70 of the aerosol generation unit 90. The heated capillary passage 70 and a heater or heating unit 72 (shown in FIG. 13) are preferably located within the aerosol generation unit 90. The first and second syringe pumps 52 and 54 are alternately communicated with the capillary passage 70 and the fluidic element 100 during their respective delivery strokes and alternately are communicated with the fluid (formulation) source during their respective drawing (aspirating) stokes, with all such actions being executed in cooperation with valves 62, 64, 66, 68. For example, as shown in FIG. 5, when the first syringe pump 52 is discharging, its output is directed along a flow path "X.sub.1" from the first syringe pump 52 to the capillary passage 70. The flow path X.sub.1 is established by closure of the valve 62 and the opening of valve 64. At the same time, the second syringe pump 54 is executing its aspirating stroke to draw fluid from the source through flow 110 along a path designated "X.sub.2". In order to establish this flow path X.sub.2, the valve 66 is opened and the valve 68 is closed.

Figure 4:
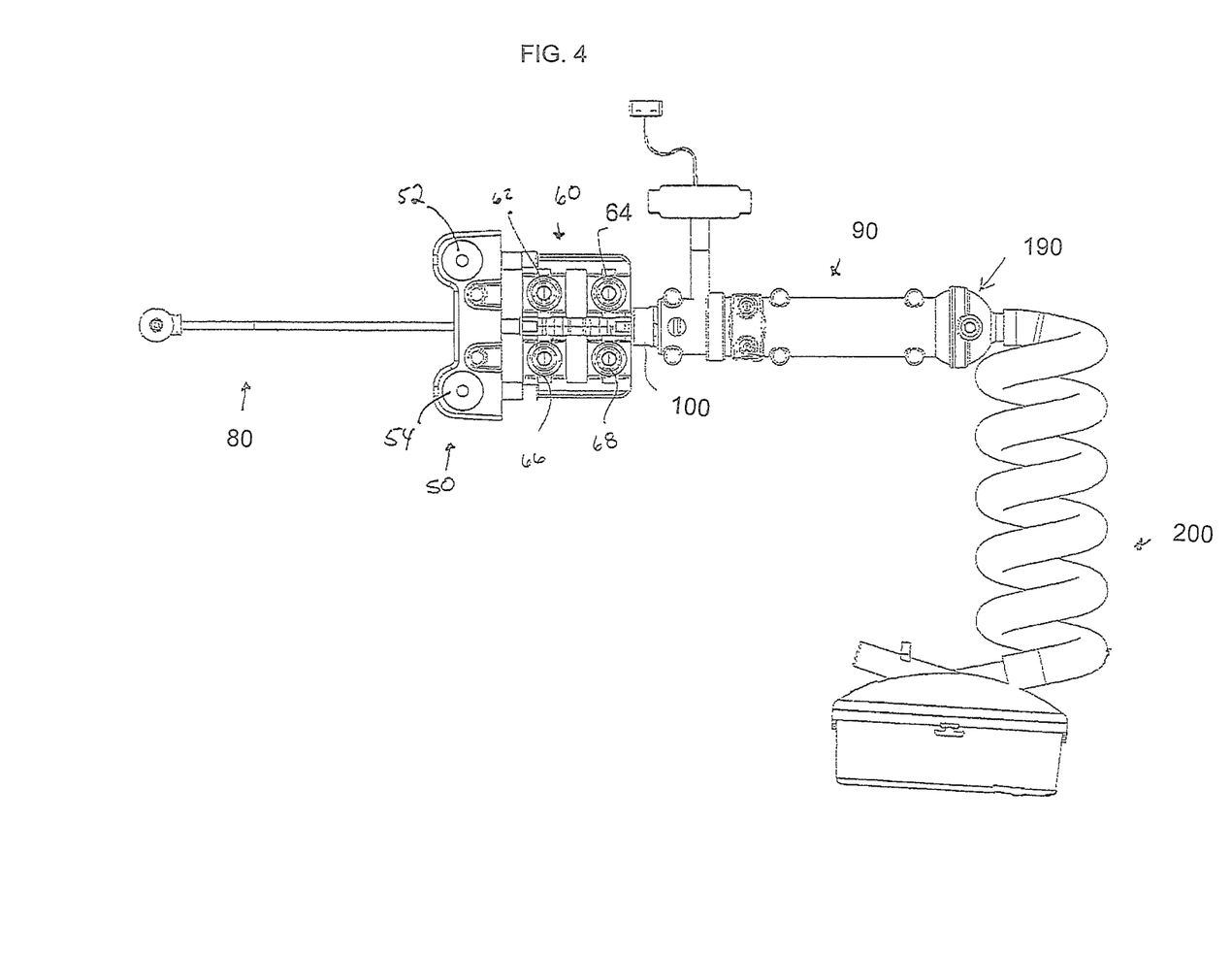
FIG. 4 is a side view of the disposable assembly of FIG. 3.

FIG. 4 is a side view of the disposable assembly 40 as shown in FIG. 3. As shown in FIG. 4, the disposable assembly 40 includes a 4-valve assembly 60, an input fluid tube assembly 80, an aerosol generation unit 90, and a fluidic element 100. The syringe pumps 52, 54 preferably include drive trains and control electronics to allow simultaneous operation of the dual syringe pumps 52, 54 in order to dispense liquid material or liquid formulation continuously. The syringe pumps 52, 54 will also preferably generate the signals for opening and closing of the valves 62, 64, 66, 68, and communicate to the programmable automation controller.

In accordance with one embodiment, the pumping unit 50 should be able to support backpressures of up to at least 2,000 psi, and more preferably up to 3,000 psi to 4,000 psi. In addition, the syringe pumps 52, 54 are preferably mounted in a fluid resistant enclosure, and can include a force sensor on each syringe-mounting bracket to monitor the plunger force during fluid delivery. The pumping capacity of the syringe pumps 52, 54 facilitate handling of highly viscous formulations such as a lung surfactant.

The aerosol generation unit 90 can include a heater or heating unit 72 in the form of a heater block assembly comprised of an upper or top assembly and a lower or bottom assembly, a thermocouple, and an aerosol generator in the form of a capillary passage or tube 70. The aerosol generation unit 90 includes a capillary passage 70 in which the liquid formulation 26 (FIG. 3) is at least partially volatilized, a heater body or block operable to heat the capillary passage 70 to a temperature range effective to at least partially volatilize liquid formulation in the capillary passage or tube 70. The capillary tube 70 can include a feed tube end or proximal end, and a domed capillary end or distal end. The capillary tube 70 preferably has an inside diameter in the range of about 0.05 to 0.53 millimeters, and more preferably in the range of about 0.1 to 0.2 millimeters. A particularly preferred inside diameter of the capillary tube 70 is approximately 0.1905 mm (or 0.0075 inches). In accordance with one embodiment, the capillary tube 70 has a length of approximately 90 mm to 120 mm, and more preferably 100 mm to 110 mm. However, it can be appreciated that the length of the capillary tube 70 is based on the flow rate of the liquid formulation or liquid material 26 within the capillary tube 70. In accordance with one embodiment, the capillary tube 70 is a tipped capillary as described in U.S. Publication No. 20050235991, the contents of which are hereby incorporated by reference in their entirety.

In accordance with one embodiment, a backpressure inducing fluidic element 100 can be introduced between the valve assembly 60 of the pumping unit 50 and the inlet of the capillary system of the aerosol generation unit 90. The fluidic element 100 introduces additional backpressure to the system 10, such that the nominal pressure or backpressure is increased above a desired threshold pressure (e.g., greater than 1200 psi). It can be appreciated that by increasing the backpressure of the system 10 above a desired threshold pressure, the fluidic element 100 provides the system 10 with a method to dampen the pressure oscillations within the system 10. In addition, the increased backpressure within the system 10 provides a means to shear the liquid formulation 26 (or liquid material) prior to entering the heated capillary tube 70, which prevents the exit orifice from becoming clogged with particles of the liquid formulation 26 having a greater diameter than the tipped capillary end.

Figure 5A:
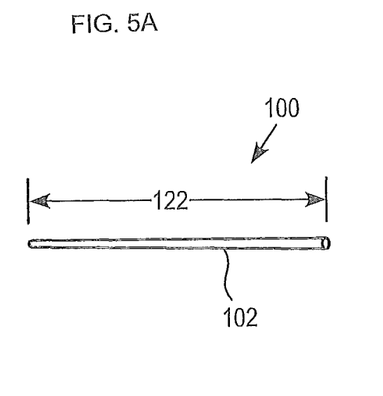
FIG. 5A is a perspective view of a fluidic element for use with the aerosol generation system of FIG. 1 in accordance with an embodiment.
Figure 5B:
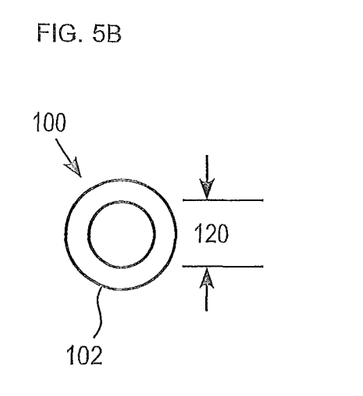
FIG. 5B is a cross-sectional view of a fluidic element in accordance with an embodiment.
Figure 6:
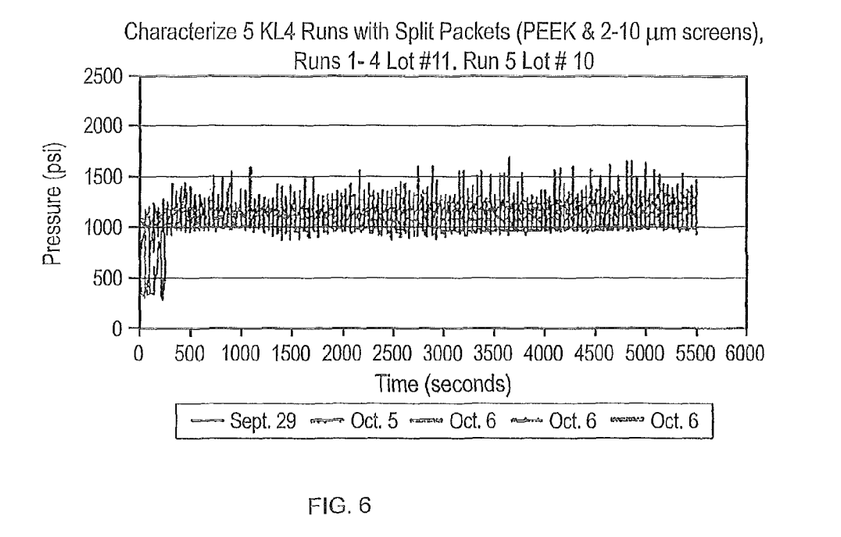
FIG. 6 is a chart of a linear fluidic element showing the backpressure within the system versus time in accordance with an embodiment.

As shown in FIGS. 5A and 5B, the fluidic element 100 is preferably a tubular member 102 having an internal diameter (ID) 120 of between approximately 0.002 to 0.010 inches, and more preferably 0.005 inches, and a length 122 of between about 4 inches to 12 inches long, and more preferably about 6 inches. In accordance with one embodiment, the fluidic element 100 preferably has a length 122 of about 4 to 12 inches, and an internal diameter of 0.002 to 0.010 inches. The fluidic element 100 preferably introduces additional backpressure into the aerosol generation system 10 from about 150 psi to 1000 psi, and more preferably about 300 psi to about 350 psi and which increases the overall operating pressure or backpressure in the system 10 during heating to about 1150 psi to about 1450 psi as shown in FIG. 6.

For example, in accordance with one embodiment, fluidic elements 100 comprised of tubular members 102 having an internal diameter 120 of 0.005 inches and 0.010 inches were implemented between the pumping unit 50 and the aerosol generation unit 90. As shown in FIG. 6, an increase in backpressure in the system 10 of 1150 psi was obtained with the addition of a fluidic element 100. With aerosolization run times of 90 minutes or more, as shown in FIG. 6, the data suggested that increasing the backpressure in the system 10 improves the overall success of the system 10 as a result of increased nominal pressure within the system and the minimization of pressure oscillations.

Figure 7:
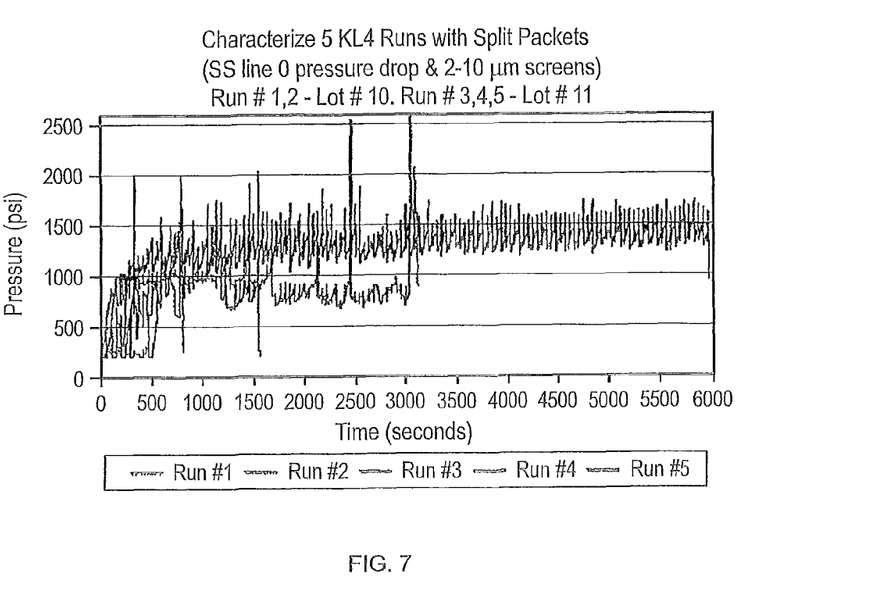
FIG. 7 is a chart showing the backpressure within the system versus time without a fluidic element.

On the contrary as shown in FIG. 7, with no additional backpressure added to system 10, the system 10 showed increased failure and the oscillations were significantly higher with the nominal operating pressure (i.e., operating pressure of the system based on the specific capillary size, including the size or diameter of the tipped capillary) or backpressure in the system being lower and more variable.

Figure 8:
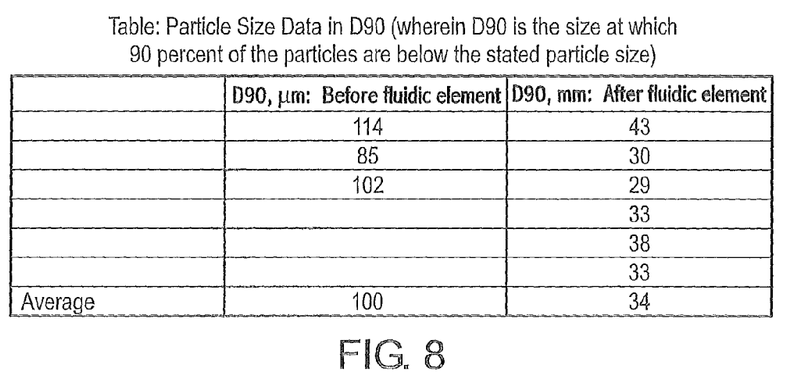
FIG. 8 is a table comparing particle size of the formulation with and without a fluidic element.

In accordance with another embodiment, as shown in FIG. 8, the fluidic element 100 can also control the particle size of the liquid formulation or liquid material 26 by shearing particles within the liquid formulation 26. For example, liquid formulations 26 having particles therein such as lung surfactant formulations can include particles of medicaments, which can exceed the size of the capillary outlet or tipped end of the capillary. Accordingly, by introducing a fluidic element 100, particles within the liquid formulation or liquid material 26 can be sheered to a particle size, which is preferably less than the diameter of the outlet, prior to the liquid formulation 26 entering the capillary passage.

Figure 9:
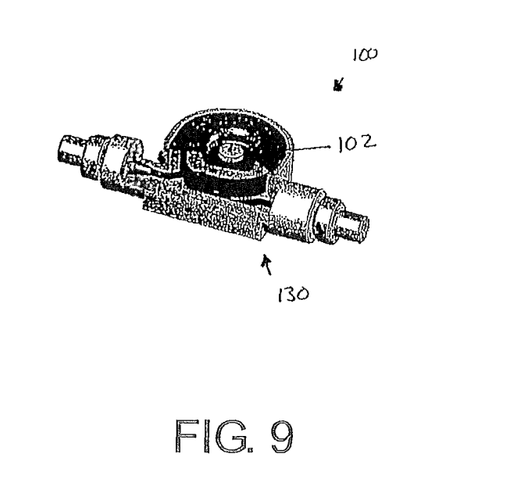
FIG. 9 is a perspective view of a fluidic element for use with an aerosol generation system in accordance with one embodiment.

It can be appreciated that the fluidic element 100 can be a linear tubular member 102 as shown in FIG. 5A, or in an alternative embodiment, the fluidic element 100 is a coiled tubular member 102, which is adapted to fit within a self-contained housing 130. As shown in FIG. 9, the fluidic element 100 can be a coiled tubular member 102, which is designed to fit within the complete delivery packet. The coiling of the tubular member 102 also increases the backpressure at the operating flow rate so that the length 120 of the tubular member 102 in a coiled format can produce different backpressure as compared to a linear tubular member 102. In accordance with another embodiment, the length 110 of the coiled tubular member 102 as compared to the linear tubular member 102 will vary to obtain a desired or optimum backpressure within the system 10.

Figure 10:
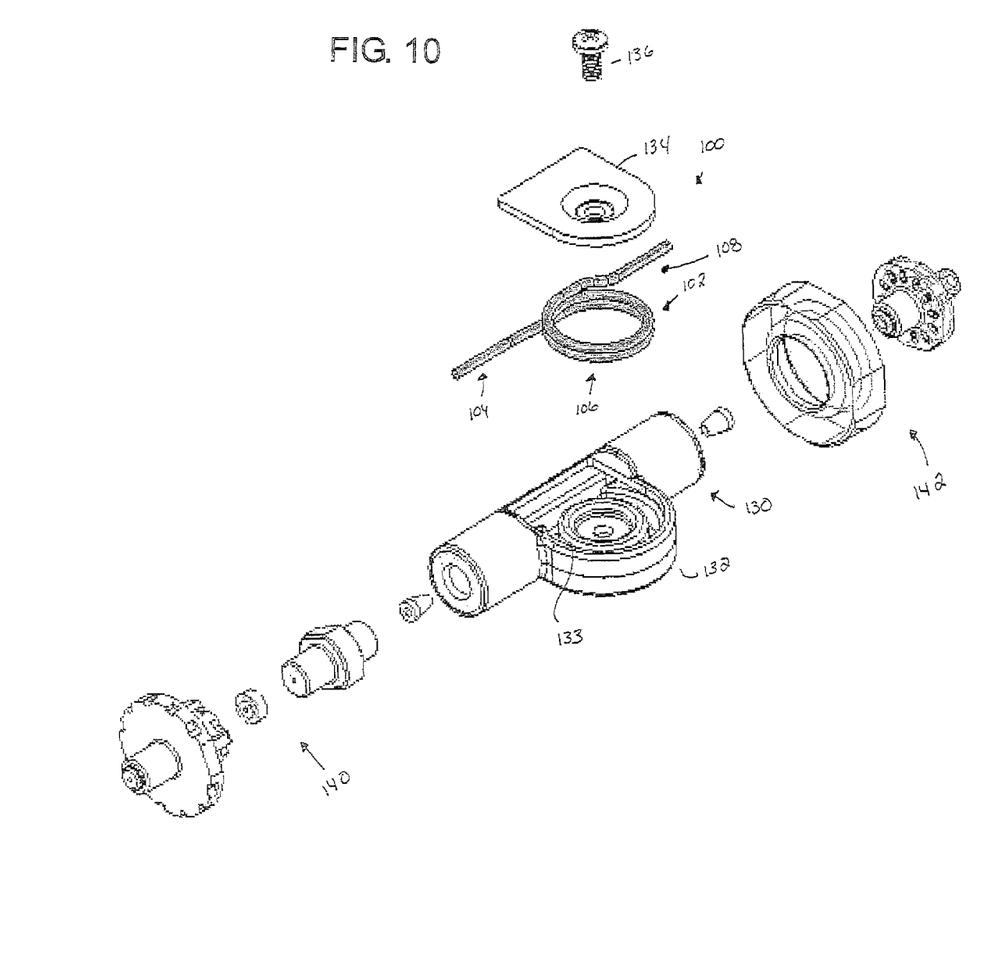
FIG. 10 is an exploded view of a fluidic element for use with an aerosol generation system in accordance with another embodiment.

FIG. 10 is an exploded perspective view of a fluidic element 100 comprised of a coiled tubular member 102 contained within a housing 130. As shown in FIG. 10, the fluidic element 100 includes a housing 130 comprised of a base unit 132 having a cavity 133 therein adapted to receive the tubular member 102, a removable cap 134 and a fastener 136 for attaching the removable cap 134 to the base unit 132. The tubular member 102 preferably includes an inlet portion 104, a coiled portion 106, and an outlet portion 108. The inlet portion 104 and the outlet portion 108 are preferably linear, however, it can be appreciated that the inlet and outlet portions 104, 108, can be angled or have a slight curve therein.

In accordance with one embodiment as shown in FIG. 10, the coiled portion 106 of the fluidic element 100 lies generally in the same plane as the inlet and outlet portions 104, 108. The length of the inlet portion 104, the coiled portion 106 and the outlet portion 108 will vary depending on the optimized backpressure desired within the system 10. The inlet portion 104 of the tubular member 102 is preferably attached to an inlet fitting assembly 140, which receives the liquid formulation 26 from the pumping unit 50 and the valve assembly 60. An outlet fitting assembly 142 connects the fluidic element 100 to the aerosol generation unit 90.

Figure 11:
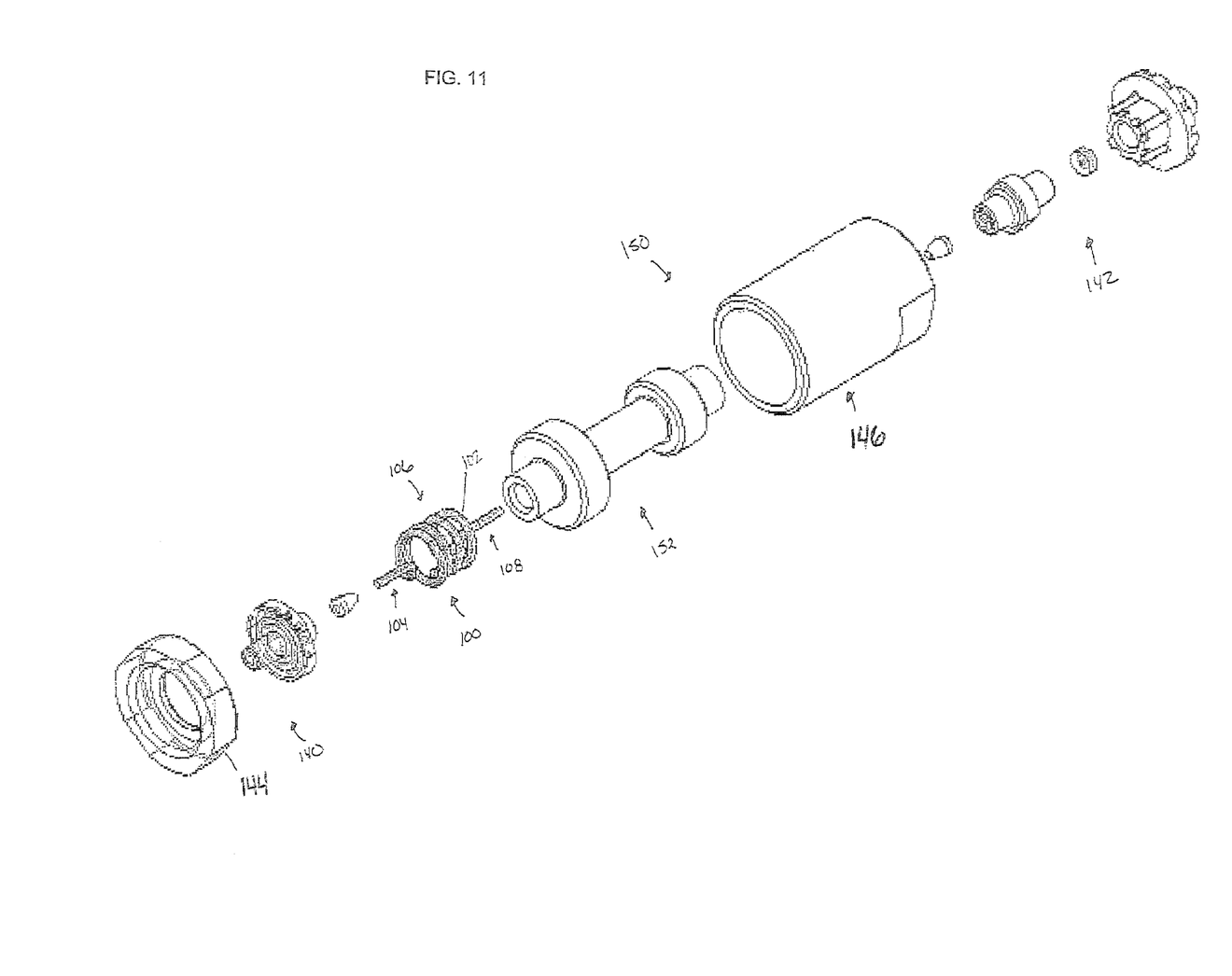
FIG. 11 is an exploded view of a fluidic element for use with an aerosol generation system in accordance with a further embodiment.

In accordance with another embodiment, as shown in FIG. 11, the coiled portion 106 of the tubular member 102 has a helical shape. The tubular member 102 also includes a generally linear inlet portion 104 and a generally linear outlet portion 108. The fluidic element 100 also has a housing 146 for the fluidic element 100 in the form of an inlet fitting assembly 142, which is adapted to fit within the housing 146. The housing 146 connects at one end to the pumping unit 50 and the valve assembly 60, and at the other end to the aerosol generation unit 90. The inlet fitting assembly 140 can include an outer ring or flange to assist with the fitting of the inlet fitting assembly 142 within the housing 146. An outlet fitting assembly 142 receives the fluidic element 100 and connects the fluidic element 100 to the aerosol generation unit 90. The housing 146 also preferably includes a threaded fastener or other suitable ring element 144 attached to the outlet fitting assembly 142.

Figure 12:
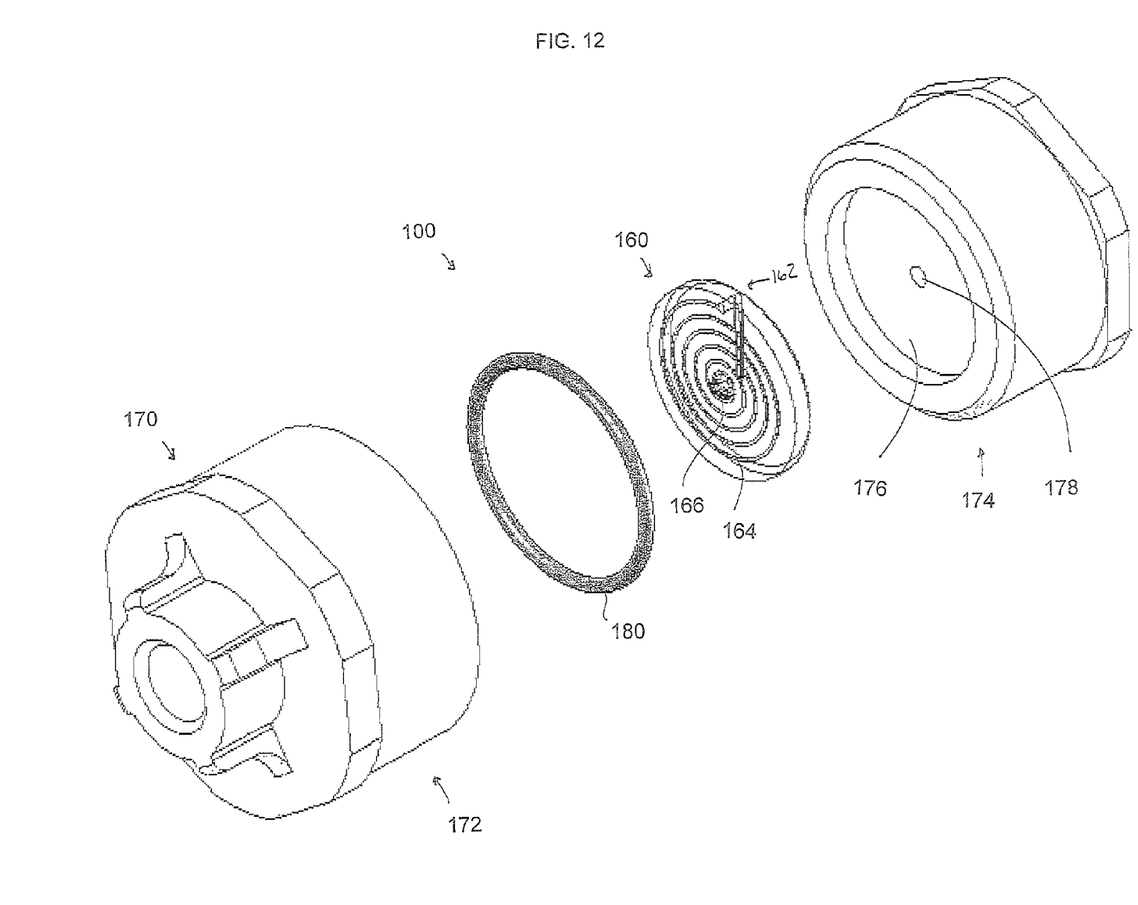
FIG. 12 is an exploded view of a fluidic element for use with an aerosol generation system in accordance with another embodiment.

In accordance with a further embodiment, as shown in FIG. 12, the fluidic element 100 can include a circular disk or plate-like element 160 having a channel 164 therein. The channel 164 is preferably in the form of a spiral having an inlet 162 adapted to receive the liquid formulation from the pumping unit 50 and the valve assembly 60. The channel 164 preferably extends from an outer portion of the circular disk or plate-like element 160 to an inner portion having an outlet 166 therein. The outlet 166 preferably extends through the circular disk or plate-like element 160 to an entrance to the capillary of the aerosol generation unit 90.

The fluidic element 100 also preferably includes a fluidic element housing 170 comprised of an outer casing member 172 and a base unit 174 having an outer distal surface 176 adapted to receive the circular disk or plate-like element 160. An O-ring or sealant ring 180 fits around an outer edge of the circular disk or plate-like element 160. The O-ring 180 is preferably an elastomeric material with a round (O-shaped) cross-section, which forms a mechanical seal for the fluidic element 100, which fits within the outer casing member 172 and the base unit 174 of the fluidic element housing 170.

FIG. 13 is a diagram of the aerosol generation system 10. As shown in FIG. 13, the aerosol generation system 10 comprises a formulation or dose packet 350, a hot plate/stirrer 300, a pumping unit 50, valve assembly 60, an aerosol generation unit 90 having a capillary tube therein, a fluidic element 100, a transition adaptor 190, and a condensate trap 200. The system 10 also can include a continuous positive airway pressure (CPAP) adaptor 310 for delivering an aerosol to a patient, an air filter 330 (such as a HEPA filter), a source of oxygen containing gas (CPAP) 320, and a control unit 340. The source of oxygen containing gas 320 is preferably from a hospital compressed airline or pressurized air source, such as a tank of compressed air with a suitable valve arrangement to achieve a desired air flow.

In accordance with one embodiment, the liquid material or liquid formulation 26, such as a lung surfactant, which is contained within a formulation or dose packet 350 is prepared for delivery to a patient by initially heating the packet 350 on the hot plate/stirrer 300 to liquefy the formulation 26 to a desired viscosity (i.e., a highly viscous formulation) for delivery to the pumping unit 50. The pumping unit 50 and the valve assembly 60 supplies the formulation 26 at a constant and continuous rate to the aerosol generator (or aerosol generation unit) 90, which includes a capillary passage in which the liquid formulation is at least partially vaporized. The heater block heats the capillary passage to a temperature range effective to at least partially volatilize liquid formulation in the capillary passage or tube into an aerosol. The aerosol generator 90 also preferably includes at least one air passage arranged such that the source of air is heated by the heater body or block, and wherein the heated or warmed air is admixed with the aerosol produced by the aerosol generator 90. It can be appreciated that the system 10 can include a separate air heater 312 in the form of a discrete air heater that is remote to the capillary tube, in lieu of or in addition to the use of the heat generated at or about the capillary tube.

The transition adaptor or aerosol confinement member 190 captures the aerosols produced by the aerosol generator 90 and the capillary tube and directs the aerosol into a flow tube for delivery to the patient via a CPAP adaptor 310. The CPAP adaptor 310 preferably delivers aerosols to the patient at about 35 to 38 degrees Celsius and more preferably about 37 degrees Celsius for infants. It can be appreciated that by varying the length of a delivery hose or tubing 104, the delivery temperature of the aerosols can be delivered at a suitable or desirable temperature. The aerosol confinement member 190 is preferably sealed to the capillary tube of the aerosol generation unit 90, which prevents ambient air (in contrast to heated air delivered to the transition adaptor) from admixing with the aerosol produced by the aerosol generator or capillary tube. The transition adaptor or aerosol confinement member 190 can include a condensate trap 200 having at least one baffle therein and/or a drainage port at a lower end thereof adapted to attach to a condensate collection device or drain tube assembly. The admixing of the heated or warm air with the aerosol produced by the formulation reduces the amount of condensation from the capillary tube to be able to deliver an aerosol to the patient located at a remote location from the system 10 and the aerosol generation unit 90.

The system 10 preferably in drug delivery applications is adapted to provide an aerosol having average mass median particle diameters of less than 2 microns to facilitate deep lung penetration. It is also desirable, in certain drug delivery applications, to deliver medicaments at high flow rates, e.g., above 1 milligram per second. It can be appreciated that the source of liquid formulation preferably contains a lung surfactant adapted for delivery as an aerosol to an infant's lungs.

While various embodiments have been described, it is to be understood that variations and modifications may be resorted to as will be apparent to those skilled in the art. Such variations and modifications are to be considered within the purview and scope of the claims appended hereto.

What is claimed is:

1. An aerosol generation system, comprising:
an aerosol generator comprising a capillary passage having an inlet and an outlet, wherein a liquid formulation is at least partially vaporized in the capillary passage and discharged from the outlet of the capillary passage to form an aerosol;
a pumping unit adapted to supply a liquid formulation to the aerosol generator; and
a fluidic element located between the pumping unit and the inlet of the capillary passage, wherein the fluidic element is adapted to introduce additional backpressure to the aerosol generation system such that the backpressure of the aerosol generation system is higher than the backpressure in an aerosol generation system not including the fluidic element.

2. The system of claim 1, wherein the fluidic element reduces particle size in the liquid formulation prior to the liquid formulation entering the capillary passage.

3. The system of claim 1, wherein the fluidic element reduces clogging of the capillary passage and/or pressure spikes within the capillary passage.

4. The system of claim 1, wherein the fluidic element is a tubular member.

5. The system of claim 4, wherein the capillary passage has a length of about 90 mm to 120 mm and the tubular member has a length of about 102 mm and 306 mm.

6. The system of claim 4, wherein the capillary passage is a capillary tube, and wherein an inner diameter of the tubular member is smaller than an inner diameter of the capillary tube.

7. The system of claim 1, wherein the fluidic element is a coiled tubular element.

8. The system of claim 7, wherein the coiled tubular element has a helical shape.

9. The system of claim 1, wherein the fluidic element is a plate-like element having a non-linear channel therein.

10. The system of claim 1, wherein the fluidic element introduces additional backpressure to the aerosol generation system from approximately 150 psi to 1000 psi.

11. The system of claim 1, wherein the capillary passage is a capillary tube having an outlet smaller in size than an inner diameter of the capillary passage and wherein the liquid formulation is at least partially vaporized by a heater block.

12. The system of claim 1, further comprising a source of liquid formulation containing a lung surfactant adapted for delivery as an aerosol to an infant's lungs.

13. The system of claim 1, wherein the fluidic element increases the back pressure of the aerosol generation system as the liquid formulation enters the inlet of the capillary passage from about 1150 psi to about 1450 psi.

14. The system of claim 1, wherein the pumping unit pumps the liquid material to the inlet of the capillary passage at a flow rate of 18 to 22 microliters per second (μl/s).

15. The system of claim 1, wherein the liquid material includes a lung surfactant and the aerosol is delivered to a CPAP oxygen containing gas delivery line.

16. The system of claim 1, wherein the outlet of the aerosol generator is a domed capillary end.

17. An aerosol generation system, comprising:
an aerosol generator comprising a capillary passage having an inlet and an outlet, wherein a liquid formulation is at least partially vaporized in the capillary passage and discharged from the outlet of the capillary passage to form an aerosol;
a pumping unit adapted to supply a liquid formulation to the aerosol generator; and
a fluidic element having a non-linear passage located between the pumping unit and the inlet of the capillary passage, wherein the fluidic element is adapted to introduce additional backpressure to the aerosol generation system such that the backpressure of the aerosol generation system is higher than the backpressure of an aerosol generation system not including the fluidic element.

18. The system of claim 17, wherein the fluidic element is a coiled tubular element.

19. The system of claim 18, wherein the coiled tubular element has a helical shape.

20. The system of claim 17, wherein the fluidic element is a plate-like element having a non-linear channel therein.

21. An aerosol generation system, comprising:
an aerosol generator comprising a capillary passage having an inlet and an outlet, wherein a liquid formulation is at least partially vaporized in the capillary passage and discharged from the outlet of the capillary passage to form an aerosol;
a pumping unit adapted to supply a liquid formulation to the aerosol generator; and
a fluidic element located between the pumping unit and the inlet of the capillary passage, wherein the fluidic element is adapted to introduce additional backpressure to the aerosol generation system such that the backpressure of the aerosol generation system is higher than the backpressure of an aerosol generation system not including the fluidic element,
wherein the capillary passage is a capillary tube, and wherein an inner diameter of the tubular member is smaller than an inner diameter of the capillary tube and wherein the capillary passage is heatable separate of the fluidic element.

* * * * *